United States Patent
Wang et al.

(10) Patent No.: US 9,685,281 B2
(45) Date of Patent: Jun. 20, 2017

(54) SAFETY MECHANISM FOR MEDICAL TREATMENT DEVICE AND ASSOCIATED METHODS

(71) Applicant: Covidien LP, Mansfield, MA (US)

(72) Inventors: Li Wang, Shanghai (CN); Chunlang Hong, Shanghai (CN); Zhen Yuan, Shanghai (CN)

(73) Assignee: Covidien LP, Mansfield, MA (US)

( * ) Notice: Subject to any disclaimer, the term of this patent is extended or adjusted under 35 U.S.C. 154(b) by 77 days.

(21) Appl. No.: 14/498,491

(22) Filed: Sep. 26, 2014

(65) Prior Publication Data

US 2015/0090575 A1  Apr. 2, 2015

(30) Foreign Application Priority Data

Sep. 29, 2013  (WO) ................ PCT/CN2013/084560

(51) Int. Cl.
*A61B 18/14* (2006.01)
*H01H 9/06* (2006.01)
(Continued)

(52) U.S. Cl.
CPC ............... *H01H 9/06* (2013.01); *A61B 18/12* (2013.01); *A61B 34/76* (2016.02); *A61B 46/10* (2016.02); *H01H 9/161* (2013.01); *A61B 2018/00178* (2013.01); *A61B 2018/00345* (2013.01); *A61B 2018/00577* (2013.01); *A61B 2018/00642* (2013.01); *A61B 2018/00702* (2013.01); *A61B 2018/00815* (2013.01); *A61B 2018/00821* (2013.01); *A61B 2018/00922* (2013.01); *A61B 2090/0807* (2016.02); *A61B 2090/0813* (2016.02); *A61B 2090/08021* (2016.02); *H01H 2221/03* (2013.01); *H01H 2223/04* (2013.01);
(Continued)

(58) Field of Classification Search
CPC .... A61B 2018/0231; A61B 2018/0091; A61B 2018/00922; A61B 2018/00928; A61B 2018/0094; A61B 2018/00946; H01H 1/36; H01H 25/002; H01H 2025/004; H01H 25/006; H01H 25/06
See application file for complete search history.

(56) References Cited

U.S. PATENT DOCUMENTS 4,006,334 A * 2/1977 Robotham et al. ........ 200/43.17
4,655,215 A    4/1987 Pike
(Continued)

FOREIGN PATENT DOCUMENTS

CN  2509465  9/2002
CN  101916675  12/2010
(Continued)

OTHER PUBLICATIONS

Extended Search Report from counterpart European Patent Application No. 14186439.7, dated Mar. 5, 2015, 7 pp.
(Continued)

*Primary Examiner* — Jaymi Della

(57) ABSTRACT

A safety mechanism for medical treatment devices includes a switch actuator that depresses a power activation switch after movement in a first direction followed movement in a second direction. The safety mechanism thus prevents accidental or unintentional delivery of power to a heating segment of the medical treatment device.

26 Claims, 8 Drawing Sheets

(51) Int. Cl.
  *H01H 9/16* (2006.01)
  *A61B 18/12* (2006.01)
  *A61B 46/10* (2016.01)
  *A61B 34/00* (2016.01)
  *A61B 18/00* (2006.01)
  *A61B 90/00* (2016.01)

(52) U.S. Cl.
  CPC ..... *H01H 2225/02* (2013.01); *H01H 2235/01* (2013.01); *H01H 2239/06* (2013.01); *H01H 2300/014* (2013.01)

(56) References Cited

U.S. PATENT DOCUMENTS

| | | | |
|---|---|---|---|
| 5,234,427 A | 8/1993 | Ohtomo et al. | |
| 5,324,193 A | 6/1994 | Pan | |
| 5,776,156 A * | 7/1998 | Shikhman | A61B 17/320016 606/167 |
| 582,996 A | 11/1998 | Ichikawa | |
| 5,868,771 A * | 2/1999 | Herbert | A61B 17/3213 30/162 |
| 5,997,282 A | 12/1999 | Man | |
| 6,216,868 B1 * | 4/2001 | Rastegar | A61B 17/3215 206/356 |
| 6,774,505 B1 * | 8/2004 | Wnuk | 307/10.8 |
| 6,887,072 B2 | 5/2005 | Judeng | |
| 7,178,244 B2 | 2/2007 | Fossella | |
| 7,300,276 B2 | 11/2007 | Sun | |
| 8,128,622 B2 | 3/2012 | Podhajsky et al. | |
| 8,172,838 B2 | 5/2012 | Schnitzler | |
| 844,954 A1 | 5/2013 | Sartor et al. | |
| 2006/0235378 A1 | 10/2006 | Waaler | |
| 2006/0286496 A1 | 12/2006 | Tu | |
| 2006/0293655 A1 * | 12/2006 | Sartor | 606/45 |
| 2009/0069805 A1 | 3/2009 | Fischer et al. | |
| 2009/0248017 A1 | 10/2009 | Heard | |
| 2009/0281377 A1 | 11/2009 | Newell et al. | |
| 2011/0269412 A1 * | 11/2011 | Bergeron et al. | 455/78 |
| 2012/0207184 A1 * | 8/2012 | Crowder et al. | 372/38.04 |
| 2012/0310227 A1 | 12/2012 | Katou | |

FOREIGN PATENT DOCUMENTS

| | | |
|---|---|---|
| CN | 202386778 | 8/2012 |
| CN | 102791212 A | 11/2012 |
| CN | 203397963 | 1/2014 |
| EP | 0655757 | 5/1995 |

OTHER PUBLICATIONS

International Search Report and Written Opinion on related PCT Application No. PCT/CN2013/084560 from International Searching Authority (SIPO) dated Jul. 16, 2014.

First Office Action, and translation thereof, from counterpart Chinese Patent Application No. 201410513076.4, dated Mar. 23, 2016, 25 pp.

* cited by examiner

SAFETY MECHANISM FOR MEDICAL TREATMENT DEVICE AND ASSOCIATED METHODS

CROSS-REFERENCE TO RELATED APPLICATIONS

The present application claims the benefit of priority under 35 U.S.C. 119 of PCT/CN2013/084560, filed Sep. 29, 2013, the contents of which are hereby incorporated by reference herein.

TECHNICAL FIELD

The present embodiments relate to medical treatment devices, and in particular to a safety mechanism for a medical treatment device.

BACKGROUND

Various medical procedures use a treatment device to apply energy to a body part of a patient. For example, two techniques currently used for endovenous treatment for venous reflux disease, as well as other diseases in hollow anatomical structures (HAS), include radio frequency ablation (RFA) and laser ablation. These techniques generally involve a treatment apparatus or system that is configured to heat tissue at a treatment site within the HAS. For example, RFA for treating venous reflux disease uses radio frequency heating to create targeted tissue ablation to seal off damaged veins. RFA equipment typically includes an RF generator and a catheter having a heating segment located at the distal end, which is inserted into the vein(s) during treatment. The heating segment uses RF energy driven by the RF generator to heat and seal the vein. RFA is also used in other medical treatments, such as, for example, arthroscopic surgery, renal denervation, and cardiac surgery.

A typical surgical RFA device comprises the RF generator, a reusable handle, and a disposable catheter having an energy application device, such as the heating segment, adjacent its distal end. The handle typically includes a button or other mechanism for initiating delivery of RF energy from the RF generator to the heating segment. It is disadvantageous and potentially dangerous for the RF energy to be accidentally or unintentionally activated, such as before the heating segment is properly placed at the treatment site. Thus, a safety mechanism is desirable on the handle.

SUMMARY

The present invention provides a safety mechanism on the switch to prevent accidental activation of the heating segment, while enabling an easy, multi-step movement for the user. The various embodiments of the present safety switch for medical treatment device and associated methods have several features. Without limiting the scope of the present embodiments as expressed by the claims that follow, their features now will be discussed briefly. After considering this discussion, and particularly after reading the section entitled "Detailed Description," one will understand how the features of the present embodiments provide the advantages described herein.

In general, in one aspect, the implementation of the disclosure features a system for medical treatment including a treatment apparatus having a proximal end and a distal end. An energy application device adjacent the distal end of the treatment apparatus, and a handle adjacent the proximal end of the treatment apparatus. The system also includes a power source, and an elongate power cable having a proximal end coupled to the power source, and a distal end coupled to the handle. A switch is within the handle, and a switch actuator is disposed on the handle and engageable with the switch. The switch actuator includes a body portion and a resilient member. The resilient member applies a retaining force to the body portion to retain the switch actuator in a ready position. A first force applied to the body portion in a direction opposite the retaining force moves the switch actuator in a direction parallel to a longitudinal axis of the handle, and a second force applied in a direction perpendicular to the retaining force moves the body portion in a direction perpendicular to the longitudinal axis of the handle and depresses the switch.

One or more of the following features may be included. When the switch is depressed, power may be delivered from the power source to the energy application device via the power cable. After the first and second forces are removed, the retaining force applied by the resilient member may return the switch actuator to the ready position. After the second force is removed, the power may continue to be delivered from the power source to the energy application device for a preset interval, and power delivery may cease after the preset interval.

The system may further include a light-emitting indicator that illuminates when the switch is depressed. The indicator may remain illuminated during the preset interval.

The switch actuator may further include a distal member positioned between the body portion and the resilient member, wherein the body portion and the distal member are separate pieces that bear against one another due to the retaining force. The switch actuator may further include a proximal member extending proximally of the body portion.

A hinge may connect the proximal member and the body portion. The hinge may be a living hinge.

The handle may include a channel that receives the switch actuator. The body portion may be disposed partially within the channel and partially outside of the channel. The switch may be disposed in a recess adjacent the channel. The switch may provide tactile feedback when the switch is depressed sufficiently to begin delivery of the power. The resilient member may be a coil spring.

In general, in another aspect, the implementation of the disclosure features a system for medical treatment including an elongate power cable having a proximal end configured for coupling to a power source, and a distal end. A handle adjacent the distal end of the power cable includes a distal end configured for coupling to a treatment apparatus. A switch is within the handle. A switch actuator is disposed on the handle and engageable with the switch. The switch actuator includes a body portion and a resilient member. The resilient member applies a retaining force to the body portion to retain the switch actuator in a ready position. A first force applied to the body portion in a direction opposite the retaining force moves the switch actuator in a direction parallel to a longitudinal axis of the handle, and a second force applied in a direction perpendicular to the retaining force moves the body portion in a direction perpendicular to the longitudinal axis of the handle and depresses the switch.

One or more of the following features may be included. When the power cable proximal end is coupled to the power source, and the handle distal end is coupled to the treatment apparatus, and the switch is depressed, power may be delivered from the power source to the treatment apparatus via the power cable. After the first and second forces are removed, the power may continue to be delivered from the power source to the treatment apparatus for a preset interval.

The system may further include a light-emitting indicator that illuminates when the switch is depressed. The indicator may remain illuminated while power is being delivered during the preset interval.

After the second force is removed, the retaining force may return the switch actuator to the ready position. The switch actuator may further include a distal member positioned between the body portion and the resilient member, wherein the body portion and the distal member are separate pieces that bear against one another due to the retaining force. The switch actuator may further include a proximal member extending proximally of the body portion.

The system may further include a hinge connecting the proximal member and the body portion. The hinge may be a living hinge.

The handle may include a channel that receives the switch actuator. The body portion may be disposed partially within the channel and partially outside of the channel. The switch may be disposed in a recess adjacent the channel. The switch may provide tactile feedback when the switch is depressed. The resilient member may be a coil spring.

In general, in another aspect, the implementation of the disclosure features a system for medical treatment including an elongate power cable having a proximal end configured for coupling to a power source, and a distal end. A handle adjacent the distal end of the power cable includes a longitudinal axis and a distal end coupled to a treatment apparatus. A switch is within the handle, and a switch actuator is disposed on the handle and engageable with the switch. The switch actuator is capable of movement along the longitudinal axis of the handle between a ready position and a firing position. When the switch actuator is in the ready position it is constrained against movement in a direction perpendicular to the longitudinal axis of the handle, and when the switch actuator is in the firing position it is capable of moving in the direction perpendicular to the longitudinal axis of the handle to depress the switch.

One or more of the following features may be included. When the power cable proximal end is coupled to the power source, and the switch is depressed, power may be delivered from the power source to the treatment apparatus via the power cable. When the switch is depressed and released, the power may continue to be delivered from the power source to the treatment apparatus for a preset interval, and after the preset interval power delivery may cease.

The system may further include a light-emitting indicator that illuminates when the switch is depressed. The indicator may remain illuminated while power is being delivered during the preset interval.

The switch actuator may further include a resilient member that biases the switch actuator toward the ready position. The switch actuator may further include a body portion and a proximal member extending proximally of the body portion.

The system may further include a hinge connecting the proximal member and the body portion. The hinge may be a living hinge.

The handle may include a channel that receives the switch actuator. The switch may disposed in a recess adjacent the channel. The switch may provide tactile feedback when the switch is depressed.

In general, in another aspect, the implementation of the disclosure features a method of medical treatment including a treatment apparatus, an energy application device adjacent a distal end of the treatment apparatus, a handle adjacent a proximal end of the treatment apparatus, a power source, an elongate power cable coupled at a proximal end to the power source and coupled at a distal end to the handle, a switch within the handle, and a switch actuator disposed on the handle and engageable with the switch, the switch actuator including a body portion and a resilient member applying a retaining force to the body portion to retain the switch actuator in a ready position. The method includes advancing the treatment apparatus into a body to be treated, and positioning the energy application device at a treatment location within the body. The method further includes applying a first force to the body portion in a direction opposite the retaining force to thereby move the switch actuator in a direction parallel to a longitudinal axis of the handle. The method further includes applying a second force to the body portion in a direction perpendicular to the retaining force to thereby move the body portion in a direction perpendicular to the longitudinal axis of the handle and depress the switch.

One or more of the following features may be included. The method may further include delivering power from the power source to the energy application device via the power cable when the switch is depressed. The method may further include removing the first and second forces from the body portion. After the first and second forces are removed, the retaining force may return the switch actuator to the ready position.

The method may further include continuing to deliver the power from the power source to the energy application device for a preset interval. The method may further include ceasing power delivery after the preset interval.

The method may further include a light-emitting indicator illuminating when the switch is depressed. The indicator may remain illuminated while power is being delivered during the preset interval.

The switch actuator may further include a proximal member extending proximally of the body portion.

The method may further include a hinge connecting the proximal member and the body portion. The hinge may be a living hinge.

The invention may be implemented to realize one or more of the following advantages. When performing a treatment procedure using an apparatus having an energy application device, such as a heating segment, it is advantageous to only provide power to the heating segment when the heating segment is positioned as desired at a treatment site. Thus, it would be advantageous to provide a safety mechanism for a medical treatment device having a heating segment to guard against accidental or unintended activation of the heating segment. The switch actuator provides an easy movement, but requires a deliberate, multi-step movement before energy may be applied to the energy application device. Various embodiments of switch actuators and associated methods are described below. For example, in certain embodiments the apparatus includes a switch actuator that must be manipulated with a combination of pushing forward in relation to the handle, and then pressing (squeezing) the switch actuator in a perpendicular direction to activate power delivery. The combination of directions makes accidental activation more unlikely, and thus makes the device safer.

BRIEF DESCRIPTION OF THE DRAWINGS

The various embodiments of the present disclosure will be discussed in detail with an emphasis on highlighting the advantageous features. These embodiments are for illustrative purposes only. These drawings include the following figures, in which like numerals indicate like parts.

DETAILED DESCRIPTION

Figure 1:
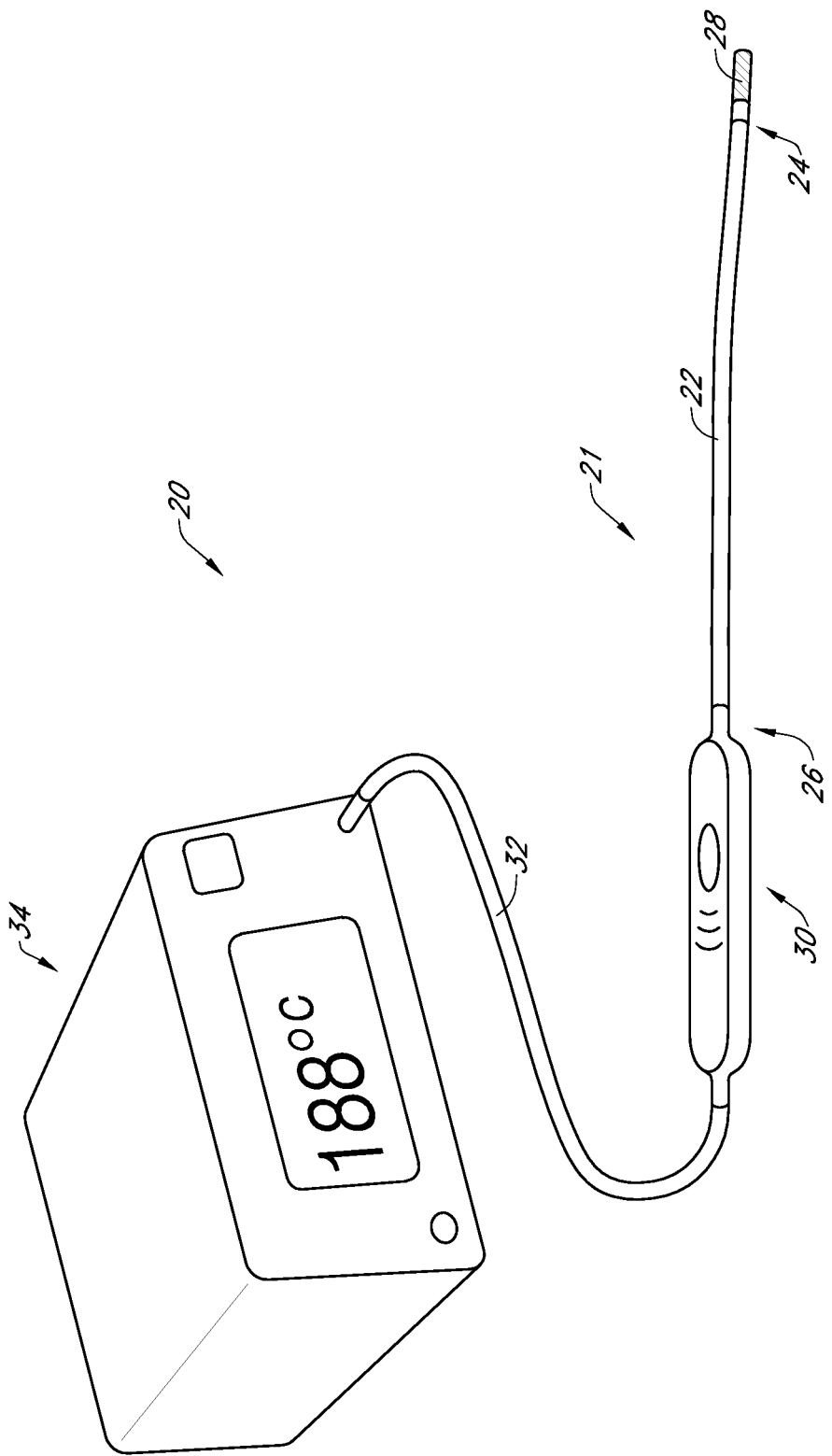
FIG. 1 is an overview of a medical treatment system.

The following detailed description describes the present embodiments with reference to the drawings. In the drawings, reference numbers label elements of the present embodiments. These reference numbers are reproduced below in connection with the discussion of the corresponding drawing features.

Directional terms used herein, such as proximal, distal, upper, lower, clockwise, counterclockwise, etc., are used with reference to the configurations shown in the figures. For example, a component that is described as rotating clockwise when viewed from the perspectives shown in the figures may be said to rotate counterclockwise when viewed from the opposite perspective. Furthermore, the present embodiments may be modified by altering or reversing the positions or directions of movement of various components. Accordingly, directional terms used herein should not be interpreted as limiting.

Referring to FIG. 1, a medical treatment system 20 may include a treatment apparatus 21 comprising a catheter shaft 22 having a distal end 24 and a proximal end 26. An energy application device, such as a heating segment 28, is operably attached adjacent the distal end 24 of the catheter shaft 22 and a handle 30 is attached at the proximal end 26 of the catheter shaft 22. The handle 30 may be integrally attached to the treatment apparatus 21, or, alternatively, the handle 30 may be removably attached to the treatment apparatus 21. A power cable 32 electrically connects the heating segment 28 to a power source 34. The power cable 32 may be integral to the handle 30 and removably connected to the power source 34. Alternatively, the power cable 32 may be removably connected to the handle 30. Alternatively, the handle 30 may comprise two sections having a first coupler portion and a second coupler portion, where the first and second coupler portions are attached to and/or integral with the power cable 32 and the treatment apparatus 21, respectively.

The heating segment 28 is secured at the distal end 24 of the elongate catheter shaft 22. The catheter shaft 22 may be used to maneuver the heating segment 28 into a desired placement within a HAS.

In certain embodiments, the power source 34 comprises an alternating current (AC) source, such as an RF generator. In other embodiments, the power source 34 comprises a direct current (DC) power supply, such as, for example, a battery, a capacitor, or other power source such as would be used for microwave heating. The power source 34 may also incorporate a controller that, through the use of a processor, applies power based at least upon readings from a temperature sensor or sensors (e.g., a thermocouple, a thermistor, a resistance temperature device, an optical or infrared sensor, combinations of the same or the like) located in or adjacent to the heating segment 28. For example, the controller may heat the tissue of a HAS or the heating segment 28 to a set temperature. In an alternative embodiment, the user selects a constant power output of the power source 34. For example, the user may manually adjust the power output relative to a temperature display from a temperature sensor in the heating segment 28.

Figure 2:
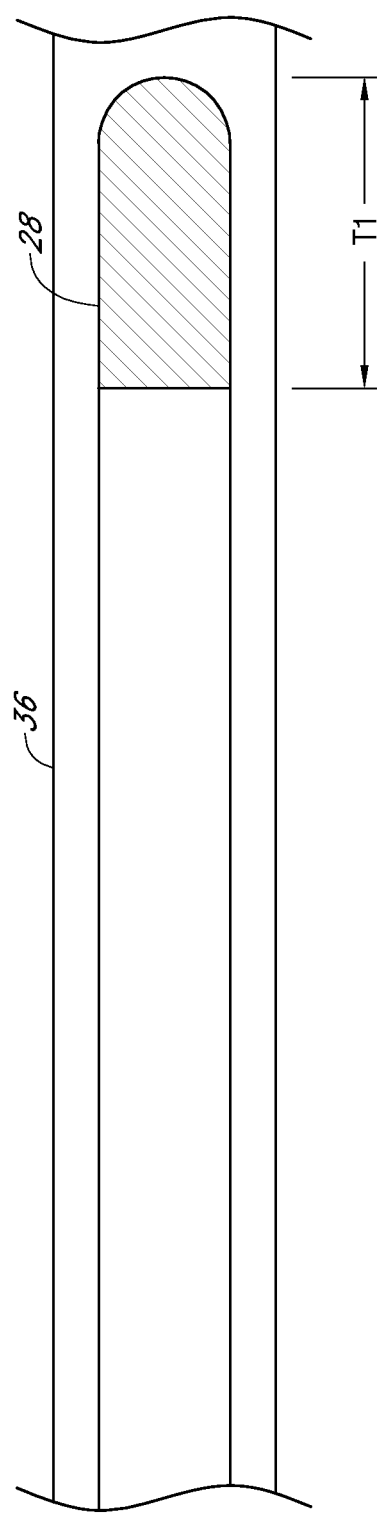
FIGS. 2 and 3 are side elevation views of an example procedure using the medical treatment system of FIG. 1.
Figure 3:
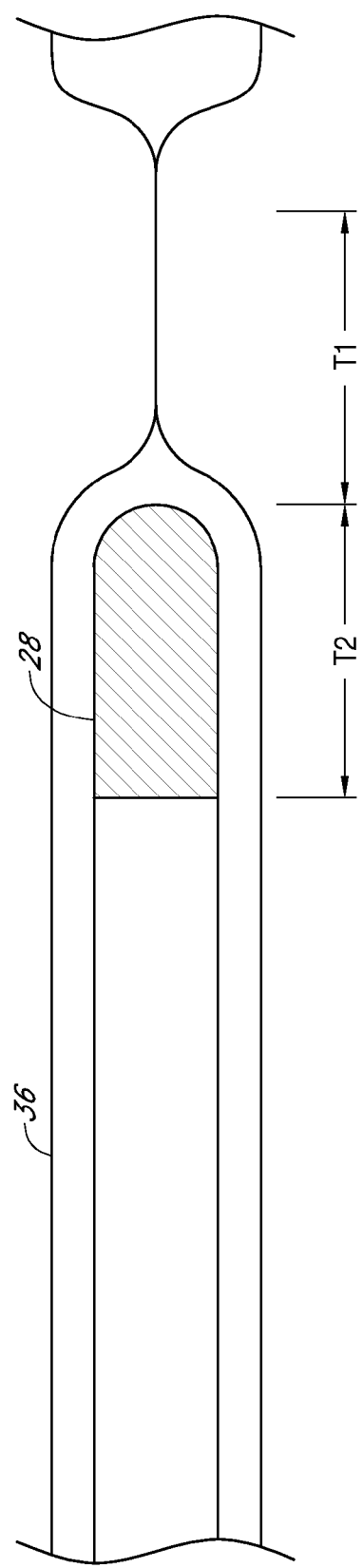

The medical treatment system 20 may be used in various medical procedures, including, for example, endovenous treatments to treat venous reflux. Specifically, referring to FIG. 2, a method may comprise inserting the heating segment 28 into a distal-most section of a HAS 36 to be treated. The heating segment 28 is then aligned with a first treatment location T1 within the HAS 36. Power is then applied to the heating segment 28 for a desired length of time to treat the first treatment location T1. After a desired dwell time, such as after the HAS 36 has collapsed as shown in FIG. 3, the power to the heating segment 28 may be reduced or shut off. With the power off (or substantially reduced), the heating segment 28 may then be moved proximally until the distal end of the heating segment 28 is adjacent to the proximal end of the first treatment location T1, as shown in FIG. 3. At this second treatment location T2 within the HAS 36, power is again applied to the heating segment 28 for a desired length of time to treat the HAS 36 at the second treatment location T2. This process of withdrawing the heating segment 28 is repeated until the treatment of the HAS 36 is complete. In some embodiments, T1 and T2 may overlap.

When performing a treatment procedure using an apparatus having a heating segment, or any other energy application device that delivers energy to a body part, it is advantageous to only provide power to the heating segment when the heating segment is positioned as desired at a treatment site. Thus, it would be advantageous to provide a safety mechanism for a treatment apparatus having a heating segment, or any other energy application device, to guard against accidental or unintended activation of the heating segment. Various embodiments of safety mechanisms and associated methods are described below. For example, in certain embodiments the apparatus includes a switch actuator that must be manipulated with a combination of pushing and then pressing (squeezing) to activate power delivery.

Figure 4:
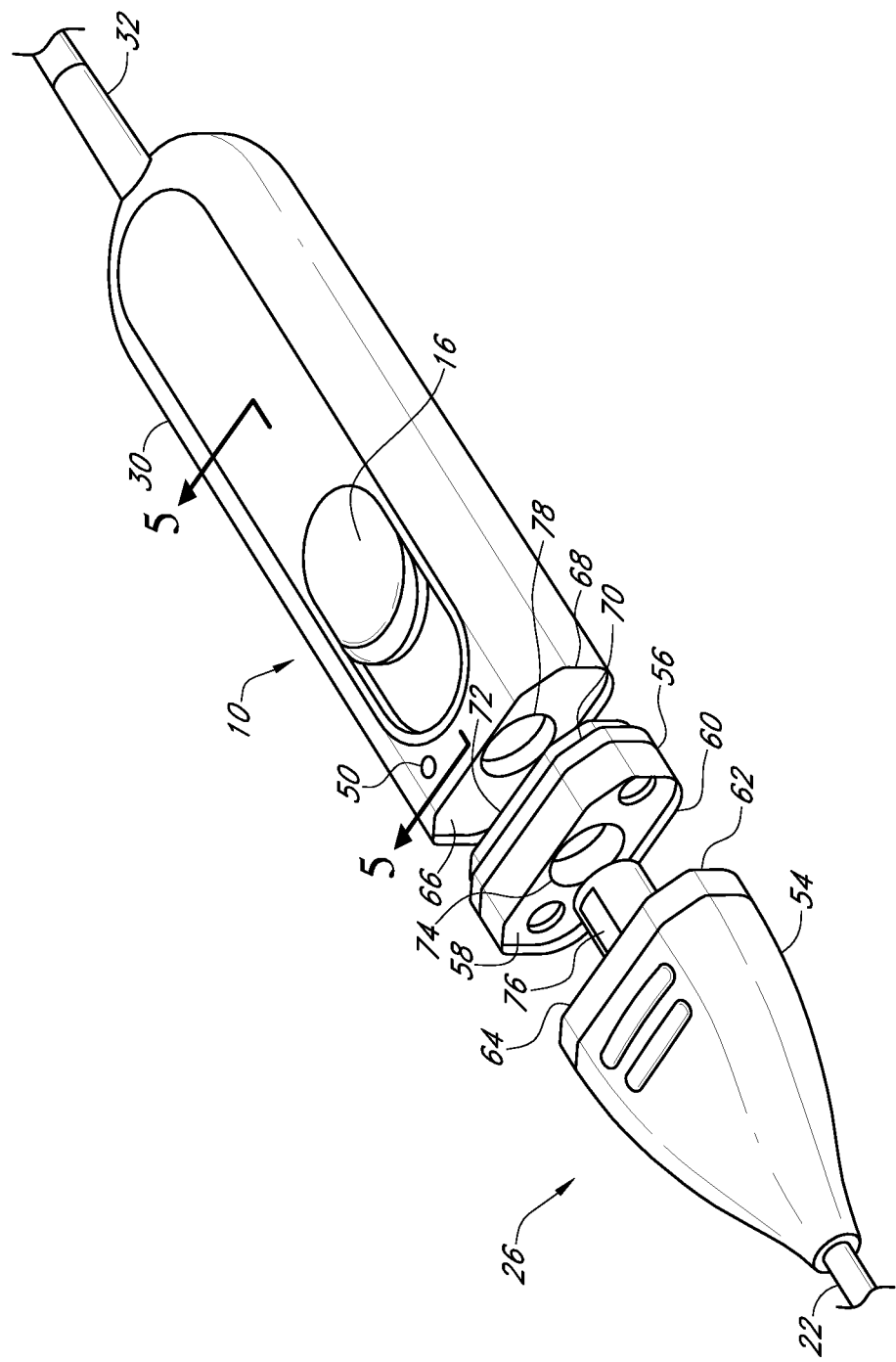
FIG. 4 is a top/front perspective view of an embodiment of a handle of a medical treatment system according to the present embodiments.
Figure 5:
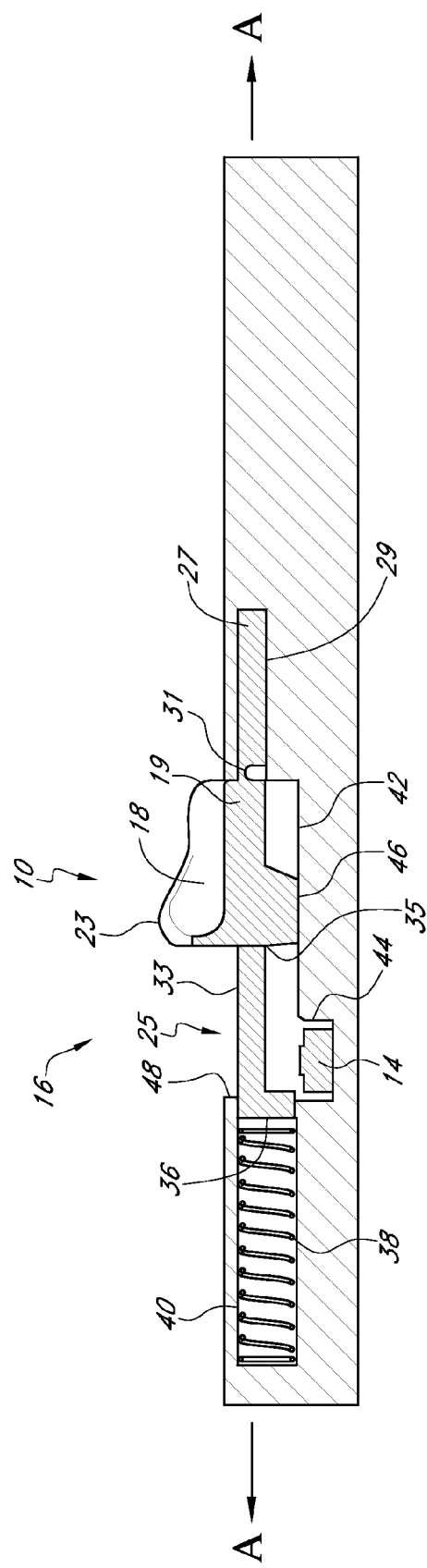
FIG. 5 is a cross-sectional side view of the handle of FIG. 4 taken along 5-5.
Figure 6:
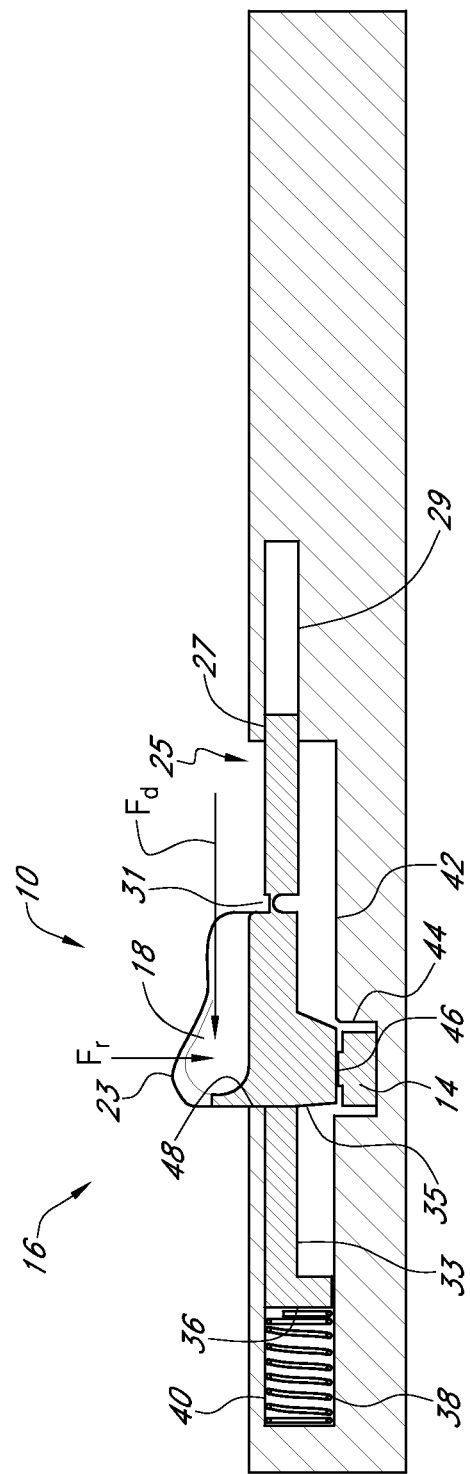
FIG. 6 is a cross-sectional side view of the handle of FIG. 4 showing the switch actuator moved distally into a firing position.

FIGS. 4-6 illustrate one embodiment of a safety mechanism for a medical treatment system to prevent accidental or unintended activation of a heating segment of the medical treatment system. In some embodiments, the system comprises the treatment apparatus 21 having a proximal end 26 and a distal end 24, the power source 34, the elongate power cable 32 having a proximal end coupled to the power source 34, and a distal end coupled to the handle 30, and an energy application device, such as the heating segment 28, adjacent the distal end 24 of the treatment apparatus 21. Examples of each of the foregoing components are described above with respect to FIG. 1, which system 20 will be used as an example system to describe the safety mechanism of the present invention.

With reference to FIG. 4, the example safety mechanism 10 is located on the handle 30 at the distal end of the power cable 32. The handle 30 includes a switch 14 (FIGS. 5 and 6) having a safety mechanism 10 that prevents accidental or unintended activation of the heating segment 28, as described below. The handle 30 further includes a switch actuator 16 that selectively engages the switch 14 to initiate power delivery from the power source 34 to the heating segment 28, as described below.

With reference to FIG. 5, the switch actuator 16 includes a body portion 18. The body portion 18 includes an inner portion 19 that resides within the handle 30 and an outer portion 23 that extends outwardly from the handle 30. The body portion 18 is located in a channel 25 that extends along the handle 30 in a direction of a longitudinal axis A of the handle 30. As further described below, the body portion 18 is slidable proximally and distally within the channel 25 along the longitudinal axis A between a ready position (FIG. 5) and a firing position (FIG. 6).

The switch actuator 16 further comprises a proximal member 27 extending proximally of the body portion 18. The proximal member 27 is received within a proximal channel extension 29 that extends proximally of the channel 25 within the handle 30. The proximal member 27 and the proximal channel extension 29 preferably have complimentary cross-sectional shapes, and the proximal channel extension 29 preferably has an inner diameter that is slightly larger than an outer diameter of the proximal member 27. The proximal member 27 is thus able to freely slide proximally and distally within the proximal channel extension 29 without substantial play between the proximal member 27 and the proximal channel extension 29.

With reference to FIG. 5, the switch actuator 16 further comprises a hinge 31 connecting the proximal member 27 and the body portion 18. The hinge 31 enables the body portion 18 to pivot with respect to the proximal member 27 such that the body portion 18 can be pushed inward to actuate the switch 14, as described below. In the illustrated embodiment, the body portion 18 and the proximal member 27 are integrally formed and the hinge 31 is a living hinge between the body portion 18 and the proximal member 27. In alternative embodiments, the body portion 18 and the proximal member 27 may be separate pieces, and the hinge 31 could comprise any other type of hinge.

The switch actuator 16 further comprises a distal member 33 that extends distally of the body portion 18. In the illustrated embodiment, the distal member 33 is a separate piece from the body portion 18, and abuts a distal face 35 of the body portion 18. A distal face 36 of the distal member 33 bears against a resilient member 38, which resides in a distal channel extension 40 that extends distally of the channel 25 within the handle 30. In the illustrated embodiment, the resilient member 38 is a coil spring, but in other embodiments the resilient member 38 could comprise any component capable of deforming in response to an applied compression force and returning to its unstressed state after the compression force is removed. Alternatively, the resilient member 38 may be attached to the proximal member 27 and anchored in the proximal channel extension 29 such that the resilient member is elongated in the axial direction in response to an applied tension force and returns to its unstressed state after the tension force is removed. In such an alternative embodiment, the distal member 33 may not be needed. Further still, the resilient member 38 may bear directly against the distal face 35 of the body portion 18. In such an embodiment, the resilient member 38 may be retained around the distal member 33, or the distal channel extension 40 may be configured to retain the resilient member 38 without the need for the distal member 33.

With reference to FIG. 5, a floor 42 of the channel 25 includes a recess 44 that is located distally of the body portion 18 when the switch actuator 16 is in the ready position shown in FIG. 5. The switch 14 occupies the recess 44. The switch 14, when depressed as described below, initiates power delivery from the power source 34 to the heating segment 28 via the power cable 32.

With continued reference to FIG. 5, the resilient member 38 applies a retaining force to the distal member 33, which in turn applies the retaining force to the body portion 18. The retaining force retains the switch actuator 16 in the ready position shown in FIG. 5. In the ready position, an inner surface 46 of the body portion 18 abuts the floor 42 of the channel 25, such that the body portion 18 cannot deflect inwardly with respect to the handle 30. However, with reference to FIG. 6, when the operator applies a distally directed force $F_d$ to the body portion 18, the body portion 18 slides distally within the channel 25 and bears against the distal member 33, displacing it distally within the distal channel extension 40 and compressing the resilient member 38, as shown in FIG. 6. Alternatively, if the resilient member 38 were attached to the proximal member 27 and anchored in the proximal channel extension 29, and the operator applies a distally directed force $F_d$ to the body portion 18, the body portion 18 slides distally within the channel 25 as does the proximal member 27, and elongates the resilient member 38.

FIG. 6 shows the switch actuator 16 in the firing position. In the firing position, the body portion 18 bears against a distal end face 48 of the channel 25 such that the body portion 18 cannot be slid any farther distally. This interaction between the body portion 18 and the distal end face 48 of the channel 25 provides tactile feedback to the operator that the switch actuator 16 is in the firing position.

In the firing position, the lower surface 46 of the body portion 18 is located above the recess 44, and therefore the body portion 18 is no longer constrained from deflecting inwardly. Thus, when the operator applies a radially inward directed force $F_r$ to the body portion 18, the body portion 18 pivots with respect to the proximal member 27 about the hinge 31 and the lower surface 46 depresses the switch 14, thereby initiating power delivery from the power source 34 to the heating segment 28 via the power cable 32. In certain embodiments, the switch 14 provides tactile feedback when the switch 14 is depressed sufficiently to begin delivery of the power. The tactile feedback indicates to the operator that power delivery has commenced.

When the operator releases both the distally directed force $F_d$ and the radially inward directed force $F_r$ from the body portion 18, the body portion 18 pivots radially outward and back to the firing position of FIG. 6 under the spring return force in the hinge 31, and then slides proximally back to the ready position of FIG. 5 under the spring return force in the resilient member 38. In certain embodiments, once power delivery commences power may continue to be delivered to the heating segment 28 for a preset interval even after the operator releases the switch actuator 16. For example, the power source 34 and/or the handle 30 may include a controller that controls the power delivery to the heating segment 28. After the preset interval has elapsed, the controller ceases the power delivery to the heating segment 28. The preset interval may be any duration.

With reference to FIG. 4, the handle 30 may include a light-emitting indicator 50 that illuminates when power delivery commences, and remains illuminated for any preset power delivery interval, after which the indicator 50 dims (and may cease emitting any light at all). The indicator 50 thus provides visual feedback to the operator, which may enhance the efficacy of treatment. In other embodiments, the indicator 50 may emit a first color, such as green, whenever power is not being delivered to the heating segment 28, and may change to a second color, such as red, whenever power is being delivered to the heating segment 28, and after power deliver ceases the indicator 50 reverts to the first color. The light-emitting indicator 50 may comprise, for example, one or more light-emitting diodes (LEDs).

Figure 4A:
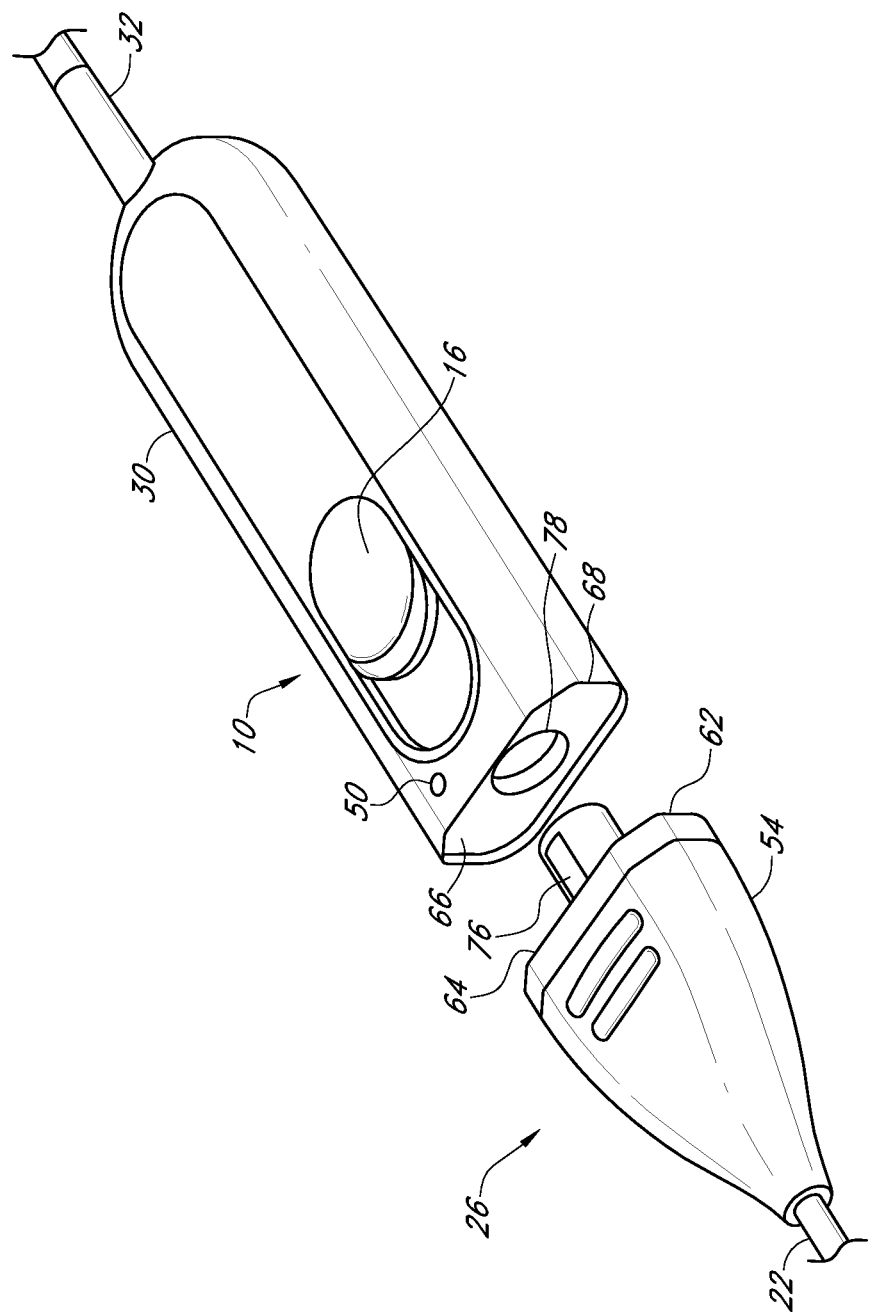
FIG. 4A is a top/front perspective view of another embodiment of a handle of a medical treatment system according to the present embodiments.

With reference to FIG. 4, a proximal end 26 of the catheter 22 includes a hub 54. A spacer 56 may interposed between the hub 54 and the handle 30. The spacer 56 has a cross-sectional shape and size that matches that of the hub 54 and the handle 30. A distal face 58 of the spacer 56 includes a raised rim 60 about its periphery that seats within a recess 62 about the periphery of a proximal face 64 of the hub 54. Similarly, a distal face 66 of the handle 30 includes a raised rim 68 about its periphery that seats within a recess 70 about the periphery of a proximal face 72 of the spacer 56. The spacer 56 includes a through hole 74 that is aligned with the longitudinal axis A of the handle 30. A post 76 extends from the proximal face 64 of the hub 54, passes through the through hole 74 in the spacer 56, and seats within an opening 78 in the distal face 66 of the handle 30 when the hub 54, the spacer 56, and the handle 30 are brought together. The post 76 engaging the through hole 74 and the opening 78 aids proper alignment of the hub 54, the spacer 56, and the handle 30, and strengthens the connection therebetween. In alternative embodiments, the post 76, the through hole 74, and/or the opening 78 may be omitted. In still further embodiments, such as shown in FIG. 4A, the spacer 56 may be omitted, and the hub 54 may be configured to be secured directly to the distal end of the handle 30. In various embodiments, any suitable method of securing the hub 54, the spacer 56, and the handle 30 to one another (or the hub 54 and the handle 30 alone) may be used, such as a snap-in tab and slot engagement, a friction fit, etc.

Figure 7:
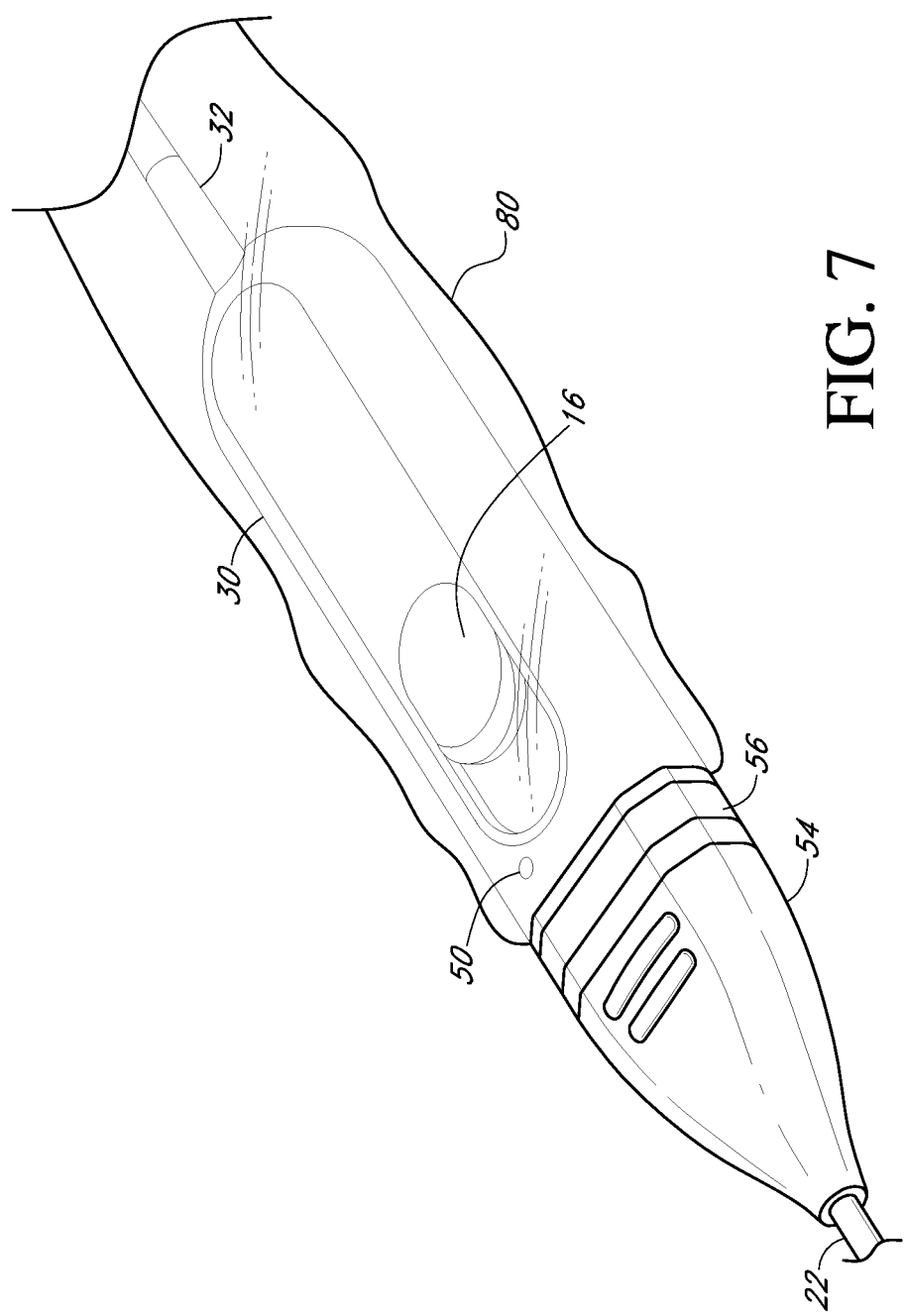
FIG. 7 is a side view of the handle of FIG. 4 with a sterile sleeve attached.

Referring now to FIG. 7, in certain embodiments, the spacer 56 serves as an attachment point for a sterile sleeve 80. As discussed above, the treatment apparatus 21 is typically a single-use device, while the handle 30 may be typically used for multiple procedures without sterilization between procedures. The sterile sleeve 80 helps to maintain sterility within the sterile field of the medical treatment procedure by covering the non-sterile components of the medical treatment system 20. For example, the sleeve 80 may be extended from its attachment point in the proximal direction to cover at least the handle 30 and also optionally at least portions of the power cable 32. The sterile sleeve 80 thus provides a sterile shield between the operator in the sterile field and the non-sterile handle 30 and power cable 32.

Certain of the present embodiments comprise a method of medical treatment including a treatment apparatus. The apparatus comprises an energy application device adjacent a distal end of the treatment apparatus, a handle adjacent a proximal end of the treatment apparatus, a power source, an elongate power cable coupled at a proximal end to the power source and coupled at a distal end to the handle, a switch within the handle, and a switch actuator disposed on the handle and engageable with the switch. The switch actuator includes a body portion and a resilient member applying a retaining force to the body portion to retain the switch actuator in a ready position.

The method comprises advancing the treatment apparatus into a body to be treated, positioning the energy application device at a treatment location within the body, applying a first force to the body portion in a direction opposite the retaining force to thereby move the switch actuator in a direction parallel to a longitudinal axis of the handle, and applying a second force to the body portion in a direction perpendicular to the retaining force to thereby move the body portion in a direction perpendicular to the longitudinal axis of the handle and depress the switch.

The method may further comprise delivering power from the power source to the energy application device via the power cable when the switch is depressed. The method may further comprise removing the first and second forces from the body portion. After the first and second forces are removed, the retaining force may return the switch actuator to the ready position. The method may further comprise continuing to deliver the power from the power source to the energy application device for a preset interval. The method may further comprise ceasing power delivery after the preset interval. The method may further comprise a light-emitting indicator illuminating when the switch is depressed. The indicator may remain illuminated while power is being delivered during the preset interval.

As described above, the present embodiments provide apparatus and methods for avoiding accidental or unintended activation of a treatment segment in a medical treatment device. To begin power delivery, the operator must first slide the switch actuator along a longitudinal axis of the handle portion, and then push the switch actuator inward in a direction perpendicular to the longitudinal axis of the handle portion. In alternative embodiments, the foregoing sequence may be reversed. That is, to begin power delivery the operator must first push the switch actuator inward in a direction perpendicular to the longitudinal axis of the handle portion, and then slide the switch actuator along a longitudinal axis of the handle portion. In yet further alternative embodiments, any sequence of two or more distinct movements must be applied to the switch actuator in order to begin power delivery. The distinct movements may be along a common axis, or along different axes.

The various components of the present embodiments may be formed of various suitable materials. For example, the handle portion, the switch actuator, the spacer, and/or the hub may be formed from any suitable biocompatible material, such as one or more polymers, metals, ceramics, etc. Non-limiting examples of polymers from which the various components may be constructed include nylon, polyethylene, polyurethane, ethylene-vinyl acetate (EVA), polyether block amide (PEBAX), acrylonitrile butadiene styrene (ABS), polyether ether ketone (PEEK), polytetrafluoroethylene (PTFE), thermoplastic polyetherimide (ULTEM), etc. Non-limiting examples of metals from which the various components may be constructed include stainless steel, titanium, cobalt-chromium, etc. Non-limiting examples of ceramics from which the various components may be constructed include porcelain, alumina, hydroxyapatite, zirconia, etc.

It is to be understood that the foregoing description is intended to illustrate and not limit the scope of the invention, which is defined by the scope of the appended claims. Other embodiments are within the scope of the following claims. For example, while the medical treatment system 20 has been described as an RFA device for treating venous reflux, the disclosed safety mechanism may be used in any medical treatment system that applies energy to a patient's body part, such as, for example, RF arthroscopic devices or cardiac catheters. Further, while the energy application device has been described as a heating segment 28, any energy application device may be used, such as, for example, direct RF energy electrodes, resistive heating coils, and microwave coils.

What is claimed is:

1. A system for medical treatment, comprising:
an elongate power cable having a proximal end configured for coupling to a power source, and a distal end;
a handle adjacent the distal end of the power cable, the handle including a distal end configured for coupling to a treatment apparatus;
a switch within the handle; and
a switch actuator disposed on the handle and engageable with the switch, the switch actuator including a body portion and a resilient member, wherein the switch actuator further comprises a proximal member extending proximally from the body portion, and a hinge connecting the proximal member and the body portion, wherein the hinge is configured to enable the body portion to pivot with respect to the proximal member,
wherein the resilient member is configured to apply a retaining force to the body portion to retain the switch actuator in a ready position, and wherein, when a first force is applied to the body portion in a direction opposite the retaining force, the switch actuator is configured to move in a direction parallel to a longitudinal axis of the handle, and wherein, when a second force is applied in a direction perpendicular to the retaining force, the body portion is configured to move in a direction perpendicular to the longitudinal axis of the handle and depress the switch.

2. The system of claim 1, wherein when the power cable proximal end is coupled to the power source, and the handle distal end is coupled to the treatment apparatus, and the switch is depressed, the power cable is configured to deliver power from the power source to the treatment apparatus.

3. The system of claim 2, wherein after the first and second forces are removed, the power cable is configured to continue to deliver the power from the power source to the treatment apparatus for a preset interval.

4. The system of claim 3, further comprising a light-emitting indicator that is configured to illuminate when the switch is depressed.

5. The system of claim 4, wherein the indicator is configured to remain illuminated while power is being delivered during the preset interval.

6. The system of claim 1, wherein after the second force is removed, the resilient member is configured to apply the retaining force to return the switch actuator to the ready position.

7. The system of claim 1, wherein the switch actuator further comprises a distal member positioned between the body portion and the resilient member, wherein the body portion and the distal member are separate pieces that are configured to bear against one another due to the retaining force.

8. The system of claim 1, wherein the hinge is a living hinge.

9. The system of claim 1, wherein the handle includes a channel that receives the switch actuator.

10. The system of claim 9, wherein the body portion is disposed partially within the channel and partially outside of the channel.

11. The system of claim 9, wherein the switch is disposed in a recess adjacent the channel.

12. The system of claim 1, wherein the switch is configured to provide tactile feedback when the switch is depressed.

13. The system of claim 1, wherein the resilient member is a coil spring.

14. The system of claim 1, wherein the hinge directly connects the proximal member and the body portion.

15. The system of claim 1, wherein the second force is applied subsequent to the first force.

16. A system for medical treatment, comprising:
an elongate power cable having a proximal end configured for coupling to a power source, and a distal end;
a handle adjacent the distal end of the power cable, the handle including a longitudinal axis and a distal end coupled to a treatment apparatus;
a switch within the handle; and
a switch actuator disposed on the handle and engageable with the switch, the switch actuator being capable of movement along the longitudinal axis of the handle between a ready position and a firing position, wherein the switch actuator comprises a body portion a proximal member extending proximally of the body portion, and a hinge connecting the proximal member and the body portion, wherein the hinge is configured to enable the body portion to pivot with respect to the proximal member,
wherein when the switch actuator is in the ready position it is constrained against movement in a direction perpendicular to the longitudinal axis of the handle, and when the switch actuator is in the firing position it is capable of moving in the direction perpendicular to the longitudinal axis of the handle to depress the switch.

17. The system of claim 16, wherein when the power cable proximal end is coupled to the power source, and the switch is depressed, the power cable is configured to deliver power from the power source to the treatment apparatus.

18. The system of claim 16, wherein when the switch is depressed and released, the power cable is configured to continue to deliver the power continues to be delivered from the power source to the treatment apparatus for a preset interval, and cease power deliver after the preset interval.

19. The system of claim 18, further comprising a light-emitting indicator that is configured to illuminate when the switch is depressed.

20. The system of claim 19, wherein the indicator is configured to remain illuminated while power is being delivered during the preset interval.

21. The system of claim 16, wherein the switch actuator further comprises a resilient member that biases the switch actuator toward the ready position.

22. The system of claim 16, wherein the hinge is a living hinge.

23. The system of claim 16, wherein the handle includes a channel that receives the switch actuator.

24. The system of claim 23, wherein the switch is disposed in a recess adjacent the channel.

25. The system of claim 16, wherein the switch is configured to provide tactile feedback when the switch is depressed.

26. The system of claim 16, wherein the hinge directly connects the proximal member and the body portion.

* * * * *